United States Patent [19]

Slavin

[11] 4,438,772
[45] Mar. 27, 1984

[54] DIFFERENTIAL STETHOSCOPE

[75] Inventor: Martin J. Slavin, Dix Hills, N.Y.

[73] Assignee: Intech Systems Corp., Hauppauge, N.Y.

[21] Appl. No.: 366,516

[22] Filed: Apr. 8, 1982

[51] Int. Cl.³ ............................................. A61B 5/02
[52] U.S. Cl. ....................................... 128/715; 381/67
[58] Field of Search .............. 128/715, 773, 680–683; 179/1 ST

[56] References Cited

U.S. PATENT DOCUMENTS

| | | | |
|---|---|---|---|
| 2,748,202 | 5/1953 | McCallister et al. | 179/171 |
| 2,902,108 | 3/1956 | Briskier | 181/24 |
| 3,020,971 | 10/1958 | Cefaly | 181/137 |
| 3,103,009 | 8/1958 | Baker | 343/17.1 |
| 3,109,508 | 2/1960 | Cefaly | 181/137 |
| 3,124,211 | 2/1960 | Cefaly | 181/131 |
| 3,126,553 | 3/1961 | Reed | 343/17.1 |
| 3,547,104 | 12/1970 | Buffington | 128/2.06 |
| 3,605,012 | 9/1971 | Kubanoff | 324/78 F |
| 3,821,948 | 7/1974 | King | 128/2.06 |
| 3,848,586 | 11/1974 | Suzuki et al. | 128/2.1 B |
| 3,978,856 | 9/1976 | Michel | 128/2.06 A |
| 4,005,701 | 2/1977 | Aisenberg et al. | 128/680 |
| 4,065,789 | 12/1977 | Devries | 358/167 |
| 4,194,511 | 3/1980 | Feldman | 128/696 |
| 4,195,360 | 3/1980 | Fothergill | 367/136 |
| 4,200,109 | 4/1980 | McMorrow, Jr. | 128/696 |
| 4,220,926 | 9/1980 | Buckner | 328/165 |
| 4,250,889 | 2/1981 | Levin | 128/708 |
| 4,261,369 | 4/1981 | Allor | 128/696 |
| 4,263,919 | 4/1981 | Levin | 128/708 |
| 4,304,240 | 12/1981 | Perlin | 128/715 X |

FOREIGN PATENT DOCUMENTS 3011770  10/1980  Fed. Rep. of Germany ...... 128/715

OTHER PUBLICATIONS

Catalog No. 14, 1977, Graham-Field Surgical Co., Inc., 4 sheets, "Grafco Mini Echo-Sounder".

Primary Examiner—Lee S. Cohen
Assistant Examiner—Francis J. Jaworski
Attorney, Agent, or Firm—Blum, Kaplan, Friedman, Silberman & Beran

[57] ABSTRACT

A portable differential stethoscope includes small microphone elements which are attached to the stethoscope heads to pick up acoustic signals from the body. The sounds picked up by the stethoscope heads include body noise signals as well as heartbeat signals. Each stethoscope head and microphone element provides an output which is amplified in an individual amplifier. The two amplified signals are inputted to separate terminals of a differential amplifier through a gain and balance control element. The differential amplifier outputs a difference signal which is amplified and inputted to an electrical headset or an electrical earphone element which is acoustically coupled to the conventional acoustic tube.

16 Claims, 3 Drawing Figures

DIFFERENTIAL STETHOSCOPE

BACKGROUND OF THE INVENTION

This invention relates generally to a stethoscope of the type used by a doctor to listen to low level signals, for example, a heartbeat, and more particularly, to a stethoscope having enhanced sensitivity for separating desired low level signals from higher ambient noise signals. Stethoscopes operating on entirely acoustic principles are well known in the art. Such stethoscopes comprise acoustic heads which are placed against the body and a pair of earpieces which are inserted in the user's ears. Between the acoustic earpieces and heads, an acoustic tube provides coupling.

The use of such instruments in detecting heartbeats is complicated by body noises produced by breathing and other body activity. Such noise can be of significantly higher levels than the heartbeat which is to be detected. Thus, the medically trained person using the stethoscope generally requests that the subject take a deep breath and hold it while the stethoscope soundings are completed. This reduces the detected lung and breathing noises and facilitates distinguishment between the heartbeat and extraneous noises.

However, it is not always possible to have the subject hold a deep breath while the medical person is listening to the heartbeat. For example, it is desirable to listen to fetal heartbeats and frequently the subject may be comatose and not responsive to requests. Many instances occur in pediatric and geriatric practice where it is not possible for the subject to refrain from breathing for the desired period of time, if at all. Also, in working with animals other than humans, it is not possible to readily eliminate the lung noises. Thus, body noises have remained a problem when a stethoscope is used in listening to a heartbeat.

What is needed is a stethoscope which isolates heartbeat signals from the noise signals and is simple in construction and operation.

SUMMARY OF THE INVENTION

Generally speaking, in accordance with the invention, a differential stethoscope especially suitable for separation of heartbeat signals from body noise signals is provided.

The differential stethoscope includes small microphone elements which are attached to the stethoscope heads to pick up acoustic signals from the body. The stethoscope heads are connected to the body at different locations where it is known that the level of heartbeat signals are different. The sounds picked up by the stethoscope heads include body noise signals as well as the heartbeat signals. Each stethoscope head and microphone element provides an output which is amplified in an individual amplifier. The two amplified signals are inputted to separate terminals of a differential amplifier through a gain and balance control element. The differential amplifier outputs a difference signal which is amplified and inputted to an electrical headset or an electrical earphone element which is acoustically coupled to the conventional acoustic tube. The tube branches out to the two earpieces as in the prior art. Terminals are provided so that outputs of the amplifiers may be displayed on an oscilloscope. The electronic circuits are housed in a small enclosure and are battery operated for ease of use and portability. Under ideal conditions, which are rarely achieved in practice, body noises such as breathing noises, which are common inputs to both microphone elements, are cancelled out in the differential amplifier, leaving clearly distinguishable heartbeat signals. The output heartbeat signals represent the difference in the heartbeat signals at each of the acoustic heads and microphone elements. In practice, the gain controls of the individual amplifiers are adjusted to most closely approach the ideal condition, with the maximum amount of body noise elimination.

Accordingly, it is an object of this invention to provide an improved stethoscope which has high sensitivity and separates heartbeat signals from other body sounds.

Another object of this invention is to provide an improved stethoscope which provides amplified output of heartbeat signals while suppressing extraneous body noises.

Another object of this invention is to provide an improved stethoscope which provides an electronically amplified output, provides filtering capabilities and is small in size.

Yet another object of the invention is to provide an improved stethoscope which provides electronically amplified signals and is light weight and compact.

Still other objects and advantages of the invention will in part be obvious and will in part be apparent from the specification.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
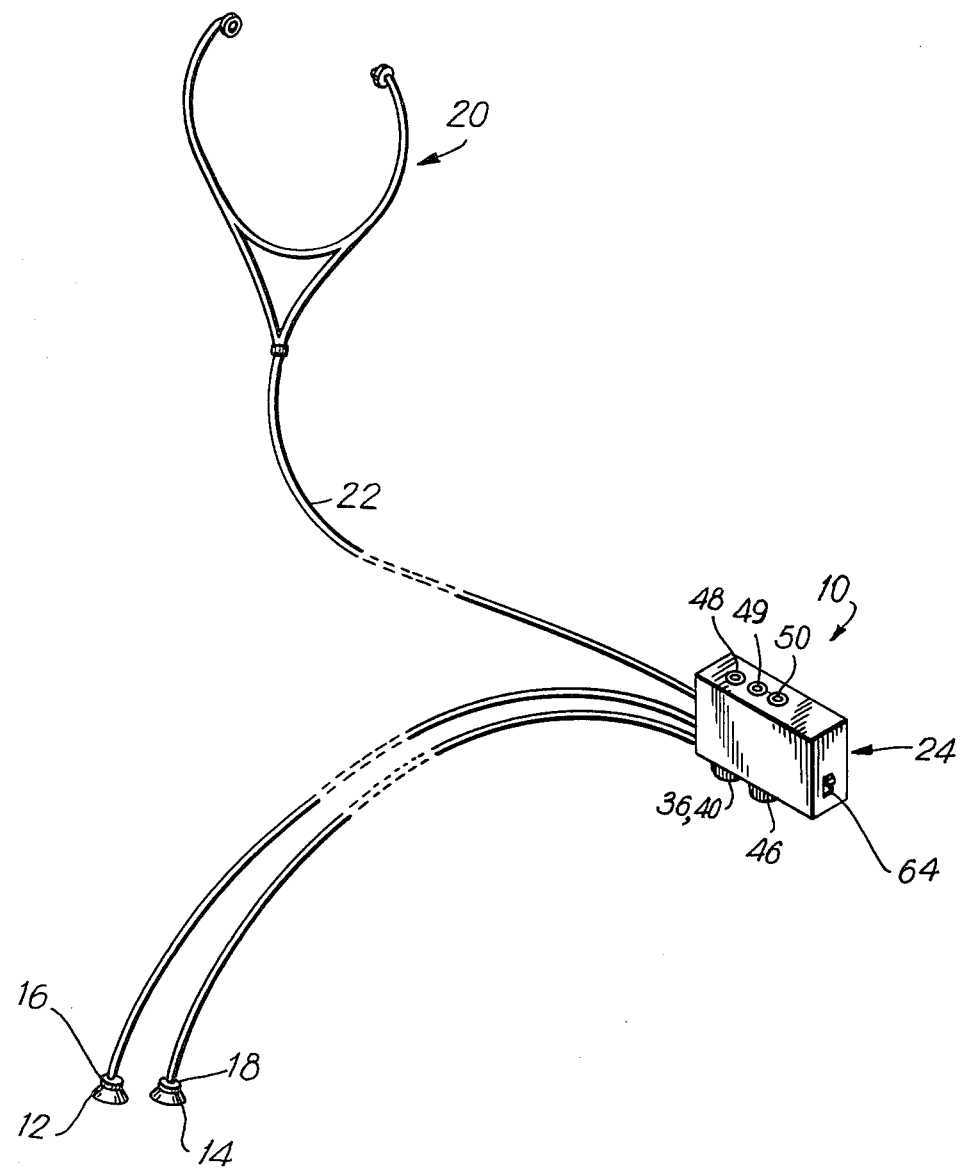
FIG. 1 is a functional schematic representation of a differential stethoscope in accordance with the invention.

With reference to FIG. 1, a differential stethoscope 10 in accordance with the invention comprises a pair of acoustic heads 12, 14 having microphone elements 16, 18 connected thereto respectively. Acoustical signals picked up by the heads 12, 14 are converted by the microphone elements 16, 18 into electrical signals suitable for input into electronical circuitry.

The differential stethoscope also includes a pair of earpieces 20, suitable for positioning in the operator's ears in the known manner and acoustic tube 22. An electronic pack 24 receives the electrical signals from the microphone elements 16, 18 and outputs selected acoustic signals to the earpieces as described more fully hereinafter.

Figure 2:
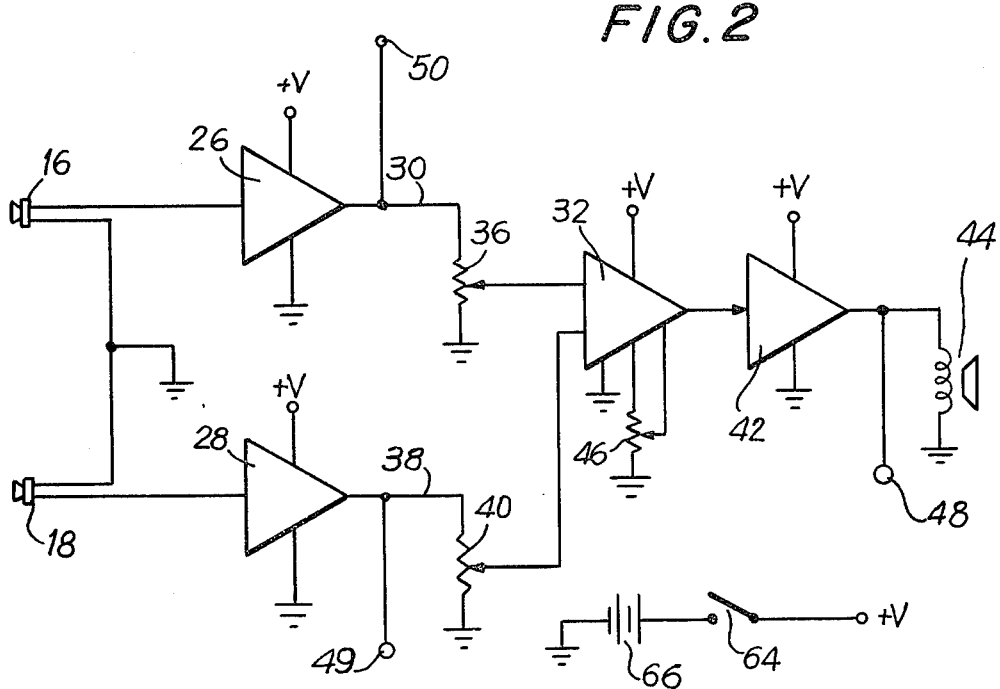
FIG. 2 is a functional schematic of the differential stethoscope of FIG. 1.

When using a differential stethoscope in accordance with the invention, in listening for a heartbeat, the microphone elements 16, 18 are positioned at different locations of the body where it is known that the amplitudes of heartbeat signals differ one from the other. An operational amplifier 26 receives the electrical signal from the microphone element 16 and provides an amplified output 30 which is input to one terminal of a differential amplifier 32. The level of signal from the amplifier 26 inputted to the differential amplifier 32 is controlled by a gain control device 36, illustrated in FIG. 2 as a resistance with a variable tapping point.

The electrical signal from the microphone element 18 is inputted to an operational amplifier 28 and the amplified output 38 is inputted to the other terminal of the differential amplifier 32 through a volume control device 40 which is similar to the device 36.

The output of the differential amplifier 32 includes the difference between the two heartbeat signals inputted respectively from the microphone elements 16, 18 and the difference between body noise signals inputted separately by the same microphone elements 16, 18. By adjustment to the gain controls 36, 40, the difference in the noise output is reduced to a minimum, ideally, zero noise output. A difference in the heartbeat signals remains since, as stated above, the microphone elements 16, 18, are at different locations on the body where heartbeat inputs are known to be different.

The output of the differential amplifier 32 is inputted to an amplifier 42 and this amplified signal is applied to an electrical headset or to an earphone element 44 which provides an acoustic input to the acoustic tube 22 (FIG. 1) and earpieces 20. Thus, heartbeat signals concealed in the body noise signals are separated from the noise by means of the differential amplifier 32 which substracts one signal from the other. The differential amplifier is adjusted for a balanced output with minimum output noise when no signals are inputted to the microphone element 16, 18 by means of a balance control 46.

Output jacks 48, 49, 50 on the electronic pack 24 connect to the outputs of the operational amplifiers 42, 28, 26, respectively, and permit display of those output signals on an oscilloscope (not shown) in the known manner.

Figure 3:
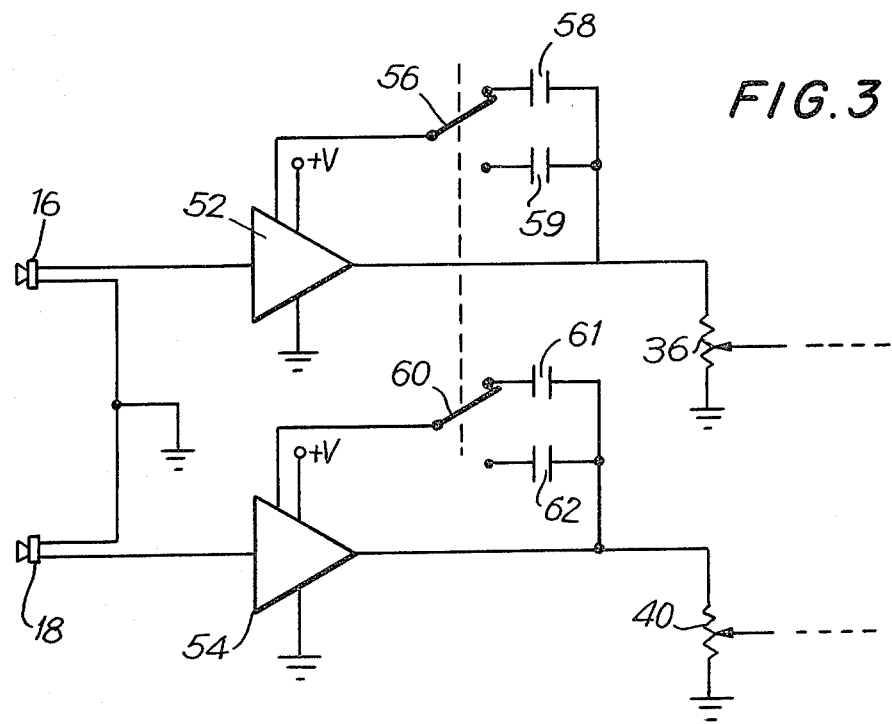
FIG. 3 is an alternative embodiment of operational amplifiers for use in the circuit of FIG. 2.

FIG. 3 illustrates an alternative embodiment of amplifiers 52, 54 respectively receiving the inputs of the microphone elements 16, 18. These operational amplifiers 52, 54 replace the operational amplifiers 26, 28 of FIG. 2. A band width switch 56 is selectively connected to one of two feedback capacitors 58, 59 connected to the operational amplifier 52. Noise signals picked up from the body are of a higher frequency content than the heart signals and the higher frequency noise components are filtered by means of a capacitance and resistances in the amplifier feedback loop in the known manner. By providing a two-step capacitor range, as illustrated in FIG. 3, a low cut-off of the higher frequency noise signals is provided for better isolation of the heartbeat signals in one position of the double throw switch 56.

The operational amplifier 54 is provided with a double throw band width switch 60 which selectively connects to one of two feedback capacitors 61, 62. The switches 56, 60 are ganged together for concurrent operation.

Gain controls 36, 40, scope jacks 48, 49, 50 and balance control 36 are externally mounted on the electronic pack 24 for operation by the user. An ON/OFF switch 60 makes and breaks the connection with an internal battery supply 66 so as to conserve power when the apparatus is not in use. A self contained power supply provides portability for the device.

Although, the above embodiments provide for an acoustic output to an earpiece or an electrical output to an electrical headset, that is, for example, earphones, it should be understood that other sensible outputs can be provided within the scope of the invention. For example, a visual output can be provided in the form of connection to a cathode ray tube oscilloscope or a simple ON/OFF illumination device may be used which responds to the heartbeat pulses. Also, a loudspeaker or buzzer device may be used to provide audible heartbeat outputs. Further, electrical outputs may be recorded in any known manner and subsequently read-out in any desired output or display.

Although the device has been described with reference to medical applications, it should be understood that many industrial applications for the same or similar device operating on the same principles exist. For example, operation of running motors, and operation of devices submerged in flowing fluids is also feasible. The circuits are simple in construction, reliable in operation, small in size, and economical to produce and operate. Use of two inputs having different levels of the desired signals and relatively equal levels of an undesired signal permits separation of the desired signal from the undesired signals through the use of a simple differential amplifier. Further selectivity may be provided when the frequencies of the two signals are substantially different by filtering, especially when the desired signal lies within a known frequency band.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also understood that the following claims are intended to cover all of the generic and specific features of the invention herein described and all statements of the scope of the invention which, as a matter of language, might be said to fall therebetween.

What is claimed is:

1. A portable stethoscope for listening to internal sounds of a body comprising:
    first and second sensor means for selective application at two selectively and variably spaced portions of the external surface of said body and for detecting said internal sounds and outputting electrical signals in response to said sounds, said sound signals including a first signal desired for detection and a second undesired signal, said first signal being masked by said second signal;
    comparison means for receiving said electrical signals from said first and second sensor means and outputting a comparison signal, said comparison signal being the difference between concurrently received electrical signals from said first and second sensor means;
    output means receiving said comparison signal and outputting a sensible signal, said sensible signal corresponding to said difference comparison signal of said detected sound signals.

2. A stethoscope as claimed in claim 1, wherein said first signal is a heartbeat signal and said second signal is derived from body noises.

3. A stethoscope as claimed in claim 2, and further comprising first and second amplifier means for receiving said electrical signals from said first and second sensor means respectively and inputting amplifier signals to said comparison means.

4. A stethoscope as claimed in claim 1 or 2, wherein said comparison means is a differential amplifier.

5. A stethoscope as claimed in claim 4, and further comprising first and second amplifier means for receiving said electrical signals from said first and second sensor means respectively and inputting amplified signals to said comparison means.

6. A stethescope as claimed in claim 5, and further comprising third amplifier means for amplifying said comparison signal, said amplified comparison signal being inputted to said sensible output means.

7. A stethoscope as claimed in claim 6, and further comprising control means for independently varying the gain of said first and second amplifier means.

8. A stethoscope as claimed in claim 7, wherein said first and second sensor means include acoustic heads and microphone means for converting acoustic signals to said electrical signals.

9. A stethoscope as claimed in claim 8, wherein said sensible output means produces at least one of an audible, visual and electrical output.

10. A stethoscope as claimed in claim 9, wherein said sensible output is audible and said output means includes one of an electrical headset and an acoustic tube with earpieces, said acoustic tube and headset being driven in response to said amplified comparison signal.

11. A stethoscope as claimed in claim 5, and further comprising band width filter means for passing said first signal and blocking at least in part said second signal.

12. A stethoscope as claimed in claim 11, wherein said second signal includes high frequencies than does said first signal, said first and second amplifier means being operational amplifiers having feedback loops including selectively variable capacitance.

13. A stethoscope as claimed in claim 12, wherein said variable capacitances of said first and second operational amplifiers are ganged for simultaneous adjustment.

14. A method of separating heartbeat sounds from a signal dominated by noise, comprising the steps:
 (a) simultaneously sensing combined heartbeat and internal noise signals at a first and a second selectively variable external body location, said heartbeat signals being of different amplitude at said first and second locations;
 (b) subtracting, one from the other, said combined signals from said first and second body locations;
 (c) outputting the difference signal produced in step b, said difference signal being dominated by the difference in said heartbeat signals from said first and second body locations.

15. A method as claimed in claim 14, and further comprising the steps:
 (1) independently amplifying said signals sensed in step (a);
 (2) prior to step (c), amplifying said difference signal produced in step (b).

16. A method as claimed in claim 15, and further comprising the step:
 (3) independently varying the amplified gain of said signals sensed in step (a) to maximize said heartbeat difference signal relative to said noise difference signal.

* * * * *